United States Patent [19]

Higgins

[11] Patent Number: 4,690,680
[45] Date of Patent: Sep. 1, 1987

[54] ADHESIVE ATTACHMENT MEANS FOR ABSORBENT ARTICLES

[75] Inventor: Maureen L. Higgins, Cincinnati, Ohio

[73] Assignee: The Procter & Gamble Company, Cincinnati, Ohio

[21] Appl. No.: 879,677

[22] Filed: Jun. 27, 1986

[51] Int. Cl.⁴ .............................................. A61F 13/16
[52] U.S. Cl. .................................... 604/386; 604/387
[58] Field of Search ............... 604/386, 387, 390, 389, 604/391

[56] References Cited

U.S. PATENT DOCUMENTS 2,295,016 9/1942 Scribner .
3,044,467 7/1962 Campau .
3,672,371 6/1972 Roeder .
3,888,255 6/1975 Shah .
4,040,424 8/1977 Hunt ..................................... 604/387
4,333,466 6/1982 Matthews .
4,445,900 5/1984 Roeder ............................. 604/390

Primary Examiner—John D. Yasko
Attorney, Agent, or Firm—John M. Pollaro; Fredrick H. Braun; Richard C. Witte

[57] ABSTRACT

An absorbent article having improved adhesive attachment means to secure the absorbent article in the crotch region of a garment. The adhesive attachments means of this invention consists of an adhesive pattern having the shape of a block "I". The block I being defined by a base portion, a stem portion, and a head portion.

20 Claims, 6 Drawing Figures

ADHESIVE ATTACHMENT MEANS FOR ABSORBENT ARTICLES

FIELD OF THE INVENTION

This invention relates generally to absorbent articles designed to be worn in the crotch region of a garment and, more particularly, to improved adhesive attachment means for such absorbent articles.

BACKGROUND OF THE INVENTION

Absorbent articles such as sanitary napkins, pantiliners, and incontinent pads are designed to absorb and retain liquid discharges from the human body and to prevent body and clothing soiling. In order to prevent soiling, such absorbent articles must be securely maintained in close proximity to and in conformity with the body of the wearer. The maintenance of the article against the body is known as "good body contact". Good body contact enables the absorbent article to absorb the vast majority of body fluids before they have an opportunity to flow quickly along the top surface of the article or the skin of the wearer, thereby preventing clothing and body soiling.

In order to securely maintain such absorbent articles in close proximity to the body of the wearer, it has become common for sanitary napkins and other absorbent articles that are designed to be worn in the crotch region of an undergarment or other garment to be secured in the crotch region by adhesive attachment means. The adhesive attachment means usually comprise a pressure sensitive adhesive disposed on the bottom surface of the article.

While absorbent articles having adhesive attachment means are convenient and comfortable, these products continue to suffer from certain disadvantages such as the risk of body and clothing soiling. It has been found that such absorbent articles are subjected to several forces during use. For example, forces are exerted on the lateral edges of the absorbent article when the article is initially placed in the garment as it conforms to the anatomical contours of the body. Movements of the wearer during walking or sitting also subject the absorbent article to applied forces such as sheer stress and torque. In addition, movements of the legs of the wearer tend to apply compression forces along the lateral and the longitudinal edges.

These applied forces during use tend to distort and bunch the center and the edges of the absorbent article, thereby causing a temporary loss of good body contact. Bunching is defined as the formation of wrinkles along either the lateral or longitudinal axes of the article. While some small amount of initial bunching along the longitudinal side edges is desirable so that the article initially creates good body contact, the resulting change in shape and wrinkles along the axes of the article brought about by bunching tend to cause the article to lose contact with the body along the troughs of the wrinkles. Body fluid can thereby easily flow along the troughs of the wrinkles resulting in an increased risk of body and garment soiling.

In addition to body and garment soiling, additional problems result from the application of forces to an absorbent article having adhesive attachment means. During movement by the wearer, the absorbent article may actually become unattached from the garment and then reattach itself. Forces which tend to distort and bunch the article also cause the article to dislodge and shift within the garment causing a loss of coverage against soiling and discomfort for the wearer. Bunching of the article may be severe enough for the article to be distorted such that the adhesive attachment means may make contact with itself and prevent the napkin from reattaching to the garment. This "sticking together" phenomenon provides less area coverage resulting in less protection against soiling and troughs that are uncomfortable for the wearer.

Several different patterns of adhesive attachment means have been developed in response to these problems. For example, U.S. Pat. No. 3,044,467 issued to Campau on July 17, 1962; U.S. Pat. No. 3,672,371 issued to Roeder on June 27, 1972; U.S. Pat. No. 3,897,783 issued to Ginocchio on Aug. 5, 1975; U.S. Pat. No. 3,888,255 issued to Shah, et al. on June 10, 1975; U.S. Pat. No. 4,333,466 issued to Matthews on June 8, 1982 and U.S. Pat. No. 4,445,900 issued to Roeder on May 1, 1984 discuss adhesive attachment patterns designed to more securely maintain a sanitary napkin within the crotch portion of the garment of the wearer.

While these patterns for adhesive attachment means serve to protect against the disadvantages caused by the applied forces, none of the structures referenced above provide the advantages of the adhesive attachment means disclosed and claimed herein. Reduced bunching and good body contact remain as key design considerations. Accordingly, adhesive attachment means providing for better securement of the article within the crotch portion of a garment while minimizing bunching and its effects have been sought.

It is, therefore, an object of the present invention to provide an absorbent article with adhesive attachment means that provide improved securement in the crotch portion of a garment.

It is another object of the present invention to provide adhesive attachment means that more securely maintains the absorbent article in close proximity to and in conformity with the body of the wearer, thereby reducing the risk of body and garment soiling.

It is a further object of the present invention to provide adhesive attachment means that will minimize bunching and distortion of the absorbent article during use.

It is a still further object of the invention to provide adhesive attachment means that will secure the article in the crotch portion of a garment while minimizing the problem of the adhesive sticking to itself during wear.

SUMMARY OF THE INVENTION

The present invention provides an absorbent article having improved adhesive attachment means to secure the absorbent article in the crotch region of a garment. The improved adhesive attachment means consists of an adhesive pattern having the shape of a block "I". The block I is defined by a base adhesive portion, a stem adhesive portion and a head adhesive portion. The base and head adhesive portions each comprises an adhesive zone located in an end region of the absorbent article. The base and head adhesive portions each may comprise one or more strips of adhesive that extend either transversely across each end region or longitudinally along the article. The stem adhesive portion comprises a longitudinally extending zone of adhesive that is centrally located with respect to the longitudinal edges of the absorbent article. The stem adhesive portion preferably comprises one or more strips of adhesive or interrupted spaced lines of adhesive. This overall block I pattern combining a base adhesive portion, a stem adhesive portion, and a head adhesive portion provides secure attachment to the crotch portion of a garment, minimizes bunching and distortion of the article during use, eliminates the possibility of the adhesive lines attaching to each other during wear, and maintains the article in close proximity to the body of the wearer so as to provide additional protection against clothing and body soiling.

While the specification concludes with claims particularly pointing out and distinctly claiming the subject matter which is regarded as forming the present invention, it is believed that the invention will be better understood from the detailed description appearing in the following section taken in conjunction with the accompanying drawings.

DETAILED DESCRIPTION OF THE INVENTION

Figure 1:
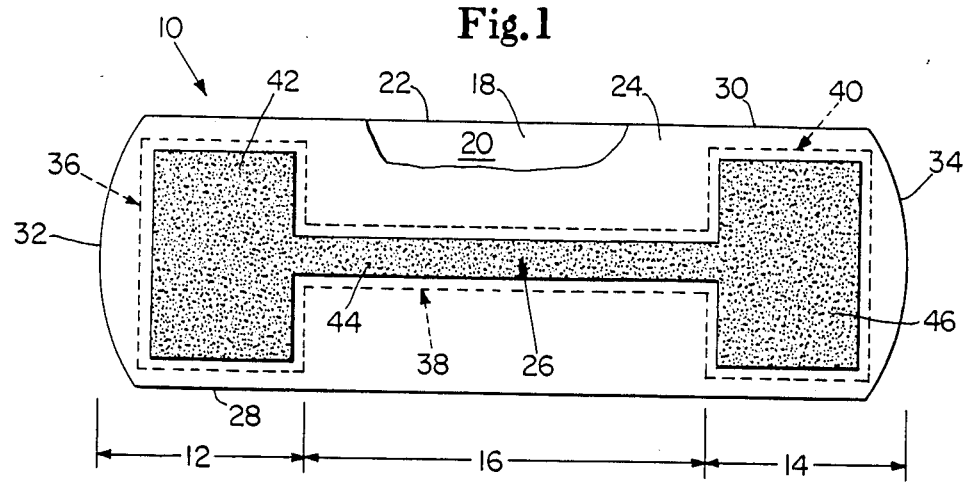
FIG. 1 is a bottom plan view of an absorbent article in accordance with the present invention with a partially cut-away section to illustrate the construction of the article.

A preferred embodiment of the disposable absorbent article of the present invention, sanitary napkin 10, is shown in FIG. 1. As used herein the term "disposable absorbent article" refers to articles which absorb and contain body exudates and more specifically refers to articles which are placed against or in proximity to the body of the wearer to absorb and contain the various exudates discharged from the body, and to articles which are intended to be discarded after a single use (i.e., they are not intended to be laundered or otherwise restored or reused). As illustrated in FIG. 1, the sanitary napkin 10 is an elongated absorbent article intended to be maintained in a woman's crotch region to absorb vaginal discharges such as menses. It should be understood, however, that the present invention is also applicable for use in other disposable absorbent articles such as incontinent pads and the like.

As shown in FIG. 1, the sanitary napkin 10 has a first end region 12, a second end region 14 and a central region 16 disposed between each of the end regions. The sanitary napkin 10 comprises an absorbent core 18 having a garment-facing side 20 and a body-facing side 22, a backsheet 24 disposed on the garment-facing side 20 of the absorbent core 12, and adhesive attachment means 26 disposed on the backsheet 24. In other preferred embodiments of the present invention, the sanitary napkin 10 can be optionally provided with additional elements as are known in the art, including a topsheet disposed on the body-facing side 22 of the absorbent core 18, a removable release liner covering the adhesive attachment means 26 in order to keep the adhesive from drying out or sticking to a surface other than the crotch portion of the garment prior to use, and wicking layers disposed between the absorbent core 18 and either the topsheet, the backsheet 24 or both.

While the sanitary napkin 10 may have any shape known in the art, a preferred embodiment of the sanitary napkin 10, which is illustrated in FIG. 1, has generally straight longitudinal edges 28 and 30 and rounded ends 32 and 34. However, any convenient design known to those skilled in the art can be used in the practice of the present invention. The sanitary napkin can, for example, have a generally hourglass shape wherein the longitudinal edges are curvilinear and the central region is narrower in the transverse direction than are the end regions. Such a design is generally illustrated in U.S. Pat. No. 4,324,246 issued to Mullane and Smith on Apr. 13, 1982. The present invention can also be used with the compound sanitary napkin described in U.S. Pat. No. 4,425,130 issued to Des Marais on Jan. 10, 1984. Further, the present invention can be used with the form of a sanitary napkin having side panels described in U.S. Pat. No. 4,285,343 issued to McNair on Aug. 25, 1981. Each of these three patents being herein incorporated by reference.

The central region 16 is that area of the sanitary napkin 10 which is generally located directly below the perineum of the wearer and which receives the greatest amount of menses. The first end region 12 and the second end region 14 extend outwardly from the central region toward the ends 32 and 34 respectively, of the sanitary napkin 10 a distance from about ⅛th to about ⅓rd of the total length of the sanitary napkin 10; although the exact size of the first and second end regions will vary according to the precise design and intended positioning of the sanitary napkin.

To provide means for absorbing body fluids, the sanitary napkin 10 is provided with an absorbent core 18. The absorbent core 18 has a garment-facing side 20 and a body-facing side 22. The absorbent core 18 may be any means which is generally compressible, conformable, nonirrating to the wearer's skin, and capable of absorbing and retaining fluids and certain body exudates. The absorbent core 18 may be formed from any of the materials well known to those of ordinary skill in the art. Examples of such materials include multiple plies of creped cellulose wadding, fluffed cellulose fibers, wood pulp fibers or comminuted wood pulp fibers which is generally referred to airfelt, textile fibers, a blend of fibers, a mass or batt of fibers, a web of polymeric fibers, a blend of polyester and polypropylene fibers, absorbent foams, absorbent sponges, superabsorbent polymers, or any equivalent material or combination of materials. The total absorbent capacity of the absorbent core should, however, be compatible with the design exudate loading and the intended use of the sanitary napkin 10. Further, the size and absorbent capacity of the absorbent core 18 may be varied. Therefore, the dimensions, shape, and configuration of the absorbent core 18 may be varied (e.g. the absorbent core 18 may have a varying caliper, or a hydrophilic gradient, or may contain superabsorbent materials).

The absorbent core 18 is preferably a mass or batt of fibers. While many types of fibers may be used, a preferred material is a batt of polyester fibers.

The backsheet 24 is associated with the absorbent core 18 and is preferably attached thereto by attachment means (not shown) such as those well known in the art. For example, the absorbent core 18 may be secured to the backsheet 24 by a uniform continuous layer of adhesive, a patterned layer of adhesive, or an array of separate lines or spots of adhesive. An adhesive which has been found to be satisfactory is manufactured by Eastman Chemical Products Company of Kingsport, Tenn. and marketed under the tradename Eastobond A-3.

While the backsheet 24 may be formed in many different ways as are known in the art, a preferred backsheet 24 is impervious to liquid and is manufactured from a thin plastic film, although other flexible liquid impervious materials may also be used. The backsheet 24 prevents the liquids absorbed and contained in the absorbent core 18 from wetting articles which contact the sanitary napkin 10 such as undergarments. Suitable materials are well known in the art, including woven and nonwoven fabrics which have been treated to render them liquid repellent. Breathable or vapor pervious, liquid resistant materials, such as those materials described in U.S. Pat. No. 3,881,489 issued to Hartwell on May 6, 1975, and U.S. Pat. No. 3,989,867 issued to Sisson on Nov. 2, 1976 can also be used. These patents are incorporated herein by reference. Preferred materials are those materials that are fluid and vapor impervious, because they provide additional fluid strikethrough protection. Especially preferable materials include formed thermoplastic films. One especially suitable material is a polyethylene film having a thickness of from about 0.075 mils to about 1.25 mils, with a 1.0 mil thickness polyethylene film being especially suitable.

The backsheet 24 may alternatively be formed from a fluid previous layer overlying a liquid imprevious layer. A preferred material for the liquid pervious material is a soft, smooth, compliant, liquid previous material as is known in the art. Those skilled in the art may readily select woven and nonwoven materials useful for this purpose, though nonwoven materials are preferred. For example, porous materials used as topsheets for disposable diapers or as coverings for conventional sanitary napkins can be used in the present invention. Useful liquid pervious layers are described in U.S. Pat. No. 4,341,217 issued to Ferguson and Landrigan on July 27, 1982, and in U.S. Pat. No. 4,342,314 issued to Radel and Thompson on Aug. 3, 1982, both patents being incorporated herein by reference.

Disposed on the backsheet 24 is the adhesive attachment means 26. The adhesive attachment means 26 are formed by coating the outer surface of the backsheet 24 with adhesive. Any adhesive or glue used in the art for such purpose can be used herein, with pressure sensitive adhesives being preferred. Suitable adhesives are Century A-305-IV manufactured by The Century Adhesive Corporation and Instant Lock 34-2823 manufactured by National Starch Company. The purpose of the adhesive attachment means 26 is to secure the sanitary napkin 10 in the crotch region of the wearer's undergarment.

The adhesive attachment means 26 consists of an adhesive pattern having the shape of a block "I". The block "I" adhesive pattern is defined as having a base adhesive portion 36 disposed in the first end region 12, a stem adhesive portion 38 centrally disposed in the central region 16, and a head adhesive portion 40 disposed in the second end region 14. It is essential that the adhesive attachment means 26 consist of all three adhesive portions so that the benefits discussed herein may be realized.

The base adhesive portion 36 is the generally rectangular zone designated by the dotted lines of FIG. 1 that is disposed in the first end region 12 of the sanitary napkin 10. The base adhesive portion 36 provides a wide adhesive area extending transversely across the first end region 12 so as to prevent shifting or bunching of the sanitary napkin 10. The base adhesive portion 36 preferably comprises a majority of the effective adhesive area available in the first end region 12. That is, the area of the base adhesive portion 36 should comprise at least about fifty percent (50%) of the effective adhesive area of the first end region 12. (The effective adhesive area being defined as that area of the other surface of the backsheet available to have adhesive applied thereto.) In addition, the base adhesive portion 36 is preferably centrally located in the first end region 12 with respect to the longitudinal edges 28 and 30 of the sanitary napkin 10. That is, the base adhesive portion 36 should be equidistantly inwardly spaced from the longitudinal edges of the sanitary napkin 10 in the first end region 12 so that adhesive does not contact the skin of the wearer. The base adhesive portion 36 should also preferably terminate before the end 32 of the first end region 12 so that adhesive will not touch the wearer. Preferably, the base adhesive portion 36 is inwardly spaced at least about 0.25 inches (about 6 mm) from the longitudinal edges 28 and 30 and at least about 0.5 inches (about 12 mm) from the end 32 in the first end region 12.

The exact adhesive pattern of the base adhesive portion 36 may widely vary and take on a number of adhesive configurations such as an array of discrete adhesive elements. For example, the base adhesive portion 36 may comprise a multiplicity of descrete adhesive elements such as adhesive strips, circles, triangles, or any other shaped adhesive pieces arranged in either a random or regular pattern which provides a wide zone of adhesive. While the size, arrangement and disposition of adhesive within the base adhesive portion may vary, the base adhesive portion 36 preferably comprises a relatively wide strip of adhesive 42 that extends transversely across the first end region 12.

The stem adhesive portion 38 is the relatively narrow rectangular adhesive zone designated by the dotted lines of FIG. 1 that is centrally disposed in the central region 16 of the sanitary napkin 10. The stem adhesive portion 38 provides a narrow adhesive area extending longitudinally in the central region 16 of the sanitary napkin 10 to allow for initial pad bunching and secure attachment of the sanitary napkin 10 in the central region 16. The stem adhesive portion 38 preferably comprises less than a majority of the effective adhesive area available in the central region 16. That is, the area of the stem adhesive portion 38 should comprise less than about 50% of the effective adhesive area and more preferably about 30% of the effective adhesive area of the central region 16. The stem adhesive portion 38 is also preferably smaller in transverse width than either the base or head adhesive portions to allow the side margins of the sanitary napkin in the central region to be void of adhesive. In additon, the stem adhesive portion 38 is preferably centrally located in the central region 16 with respect to the longitudinal edges 28 and 30 of the sanitary napkin 10. That is, the stem adhesive portion 38 should be equidistantly inwardly spaced from the longitudinal edges 28 and 30 of the sanitary napkin 10. Preferably, the stem adhesive portion 38 is disposed at least about 0.75 inches (about 18 mm) from the narrowest point of each longitudinal edge of the sanitary napkin 10 in the central region 16.

The exact adhesive pattern of the stem adhesive portion 38 may widely vary and take on a number of adhesive configurations such as an array of discrete adhesive elements. For example, the stem adhesive portion 38 may comprise a multiplicity of discrete adhesive elements such as adhesive strips, circles, triangles, or any other shaped adhesive pieces arranged in either a random or regular pattern which provide a narrow zone of adhesive. It should be noted that the adhesive elements that comprise the stem adhesive portion 38 may also serve as portions of either the base or head adhesive within the stem adhesive portion 38 may vary, the stem adhesive portion 38 preferably comprises a relatively narrow strip of adhesive 44 centrally disposed with respect to the longitudinal edges of the sanitary napkin and extending longitudinally along the sanitary napkin.

The head adhesive portion 40 is the generally rectangular zone designated by the dotted lines of FIG. 1 that is disposed in the second end region 14 of the sanitary napkin 10. The head adhesive portion 40 provides a wide adhesive area extending transversely across the second end region 14 so as to prevent shifting or bunching of the sanitary napkin 10. The head adhesive portion 40 preferably comprises a majority of the effective adhesive area available in the second end region 14. That is, the area of the head adhesive portion 40 should comprise at least about fifty percent (50%) of the effective adhesive area of the second end region 14. In addition, the head adhesive zone 40 is preferably centrally located in the second end region 14 with respect to the longitudinal edges 28 and 30 of the sanitary napkin 10. That is, the head adhesive portion 40 should be equidistantly inwardly spaced from the longitudinal edges 28 and 30 of the sanitary napkin in the second end region 14 so that adhesive does not contact the skin of the wearer. The head adhesive portion 40 should also preferably terminate before the end edge 34 of the second end region 14 so that adhesive will not touch the wearer. Preferably, the head adhesive portion 40 is inwardly spaced at least about 0.25 inches (about 6 mm) from the longitudinal edges 28 and 30 of the sanitary napkin 10 in the second end region 14 and at least about 0.5 inches (about 12 mm) from the second end 30.

The exact adhesive pattern of the head adhesive portion 40 may widely vary and take on a number of adhesive configurations such as an array of discrete adhesive elements. For example, the head adhesive portion 40 may comprise a multiplicity of discrete adhesive elements such as adhesive strips, circles, triangles or any other shaped adhesive pieces arranged in either a random or regular pattern which provides a wide zone of adhesive. While the size, arrangement and disposition of adhesive within the head adhesive portion 40 may vary, the head adhesive portion 40 preferably comprises a relatively wide strip of adhesive 46 that extends transversely across the second end region 14. While the head adhesive portion 40 preferably comprises the same adhesive pattern as the base adhesive portion 36, it should be understood that the head adhesive portion 40 may comprise a different adhesive pattern than that of the base adhesive portion 36.

While not wishing to be bound by theory, it is believed that a centrally located zone of adhesive, stem adhesive portion 38, in conjunction with a pair of adhesive zones, one of which is located in each end region, head adhesive portion 40 and base adhesive portion 36, tends to distribute the forces applied to a sanitary napkin or other absorbent article over the length of the napkin. Such adhesive attachment means 26 is especially resistant to torque and sheer stress during use because it is believed that the part of the napkin along the longitudinal side edges in the central region is allowed to stretch and conform to the forces applied during initial placement and use to maintain good body contact, while the central portion of the central region and the end regions are securely attached to prevent shifting or bunching. Therefore, the napkin initially conforms to the body of the wearer because of the lack of adhesive along the longitudinal side edges, remains securely in place providing good body contact that minimizes the risk of soiling, and does not shift thereby being more comfortable for the wearer. In addition, head adhesive portion 40 and base adhesive portion 36, while disposed near the ends of the napkin where there exists a possibility of the adhesive sticking together, is not likely to fold over and stick to itself during use because of the secure attachment of the central portion of the napkin provided by the stem adhesive portion 38.

In use, the sanitary napkin 10 is secured on the inside of the crotch portion of a garment with the adhesive side toward the crotch. It is secured in position by pressing the adhesive attachment means 26 firmly against the crotch material. The adhesive is entirely within the margin of the sanitary napkin, so that there is no possible contact with the body of the wearer.

Figure 2:
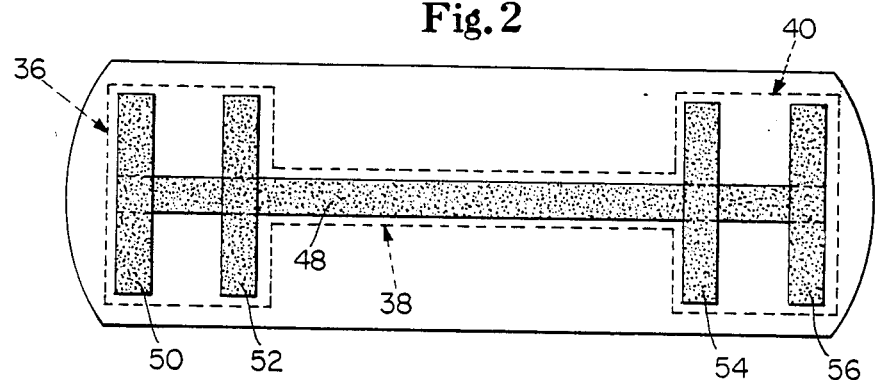
FIG. 2 is a bottom plan view of an alternative embodiment of the absorbent article of the present invention.

FIG. 2 shows an alternative embodiment of the sanitary napkin of the present invention. The stem adhesive portion 38 comprises a segment of a relatively narrow strip of adhesive 48 that extends longitudinally along the sanitary napkin 10. The base adhesive portion 36 and the head adhesive portion 40 each comprises two relatively narrow strips of adhesive 50, 52 and 54, 56, respectively, that extend transversely across each of the end regions of the sanitary napkin and a segment of the strip of adhesive 48 that extends into each of the end regions.

Figure 3:
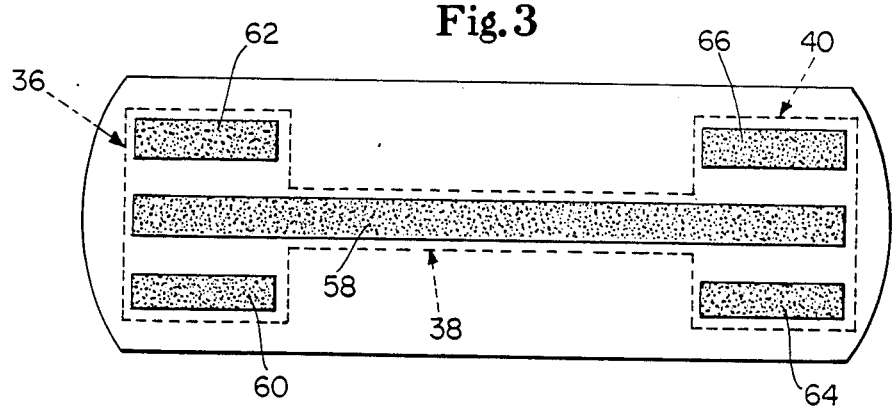
FIG. 3 is a bottom plan view of another alternative embodiment of the absorbent article of the present invention.

FIG. 3 shows another alternative embodiment of the sanitary napkin of the present invention. The stem adhesive portion 38 comprises a segment of a relatively narrow strip of adhesive 58 that extends longitudinally along the sanitary napkin 10. The base adhesive portion 36 and the head adhesive portion 40 each comprises at least two relatively narrow lines or strips of adhesive 60, 62 and 64, 66, respectively, that extend longitudinally along the sanitary napkin in the end regions and a segment of the strip of adhesive 58 that extends into the end regions.

Figure 4:
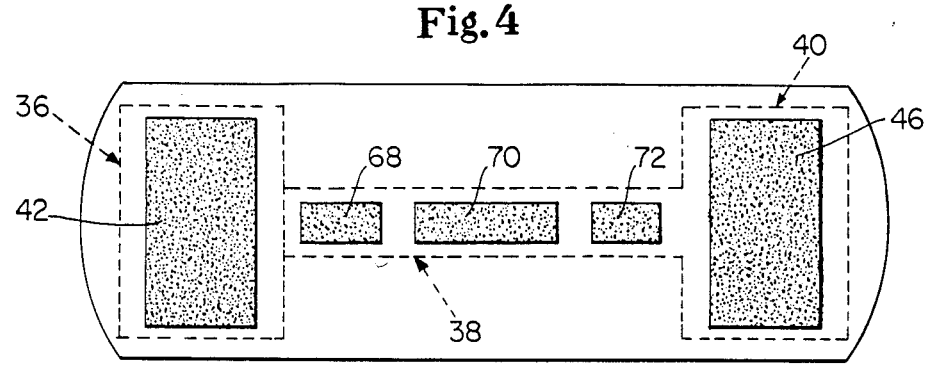
FIG. 4 is a bottom plan view of an alternative embodiment of the absorbent article of the present invention.

FIG. 4 shows an alternative embodiment of the sanitary napkin of the present invention. The stem adhesive portion 38 comprises discrete spaced strips 68, 70 and 72 of adhesive. The individual spaced adhesive strips 68, 70 and 72 extend longitudinally along the sanitary napkin. While not being bound by theory, it is believed that a discontinuous line of adhesive such as disclosed in FIG. 4 allows the sanitary napkin to stretch and conform more closely with the stretch of the supporting garment, thereby minimizing bunching of the sanitary napkin. The base adhesive portion 36 and the head adhesive portion 40 each comprises a relatively wide single strip of adhesive 42 and 46 that extends transversely across each end of the end regions of the sanitary napkin.

Figure 5:
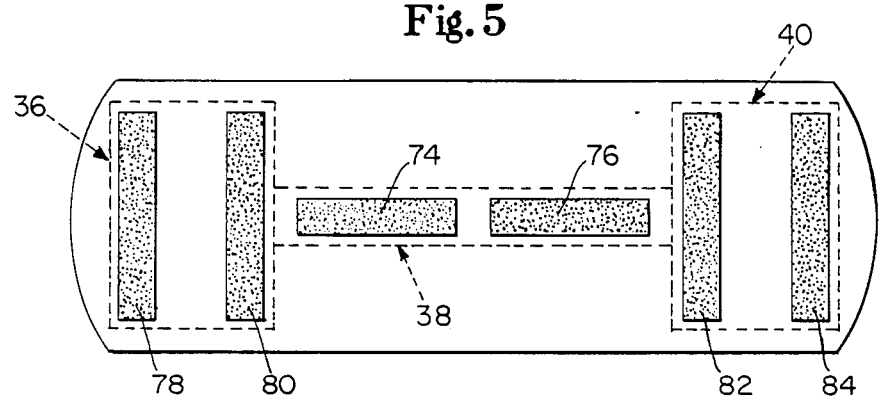
FIG. 5 is a bottom plan view of a further alternative embodiment of the absorbent article of the present invention.

FIG. 5 shows a further alternative embodiment of the sanitary napkin of the present invention. The stem adhesive portion 38 comprises interrupted space adhesive strips 74 and 76 that extend longitudinally along the sanitary napkin. The base adhesive portion 36 and the head adhesive portion 40 each comprises two narrow strips of adhesive 78, 80 and 82, 84, respectively, that extend transversely across each of the end regions of the sanitary napkin.

Figure 6:
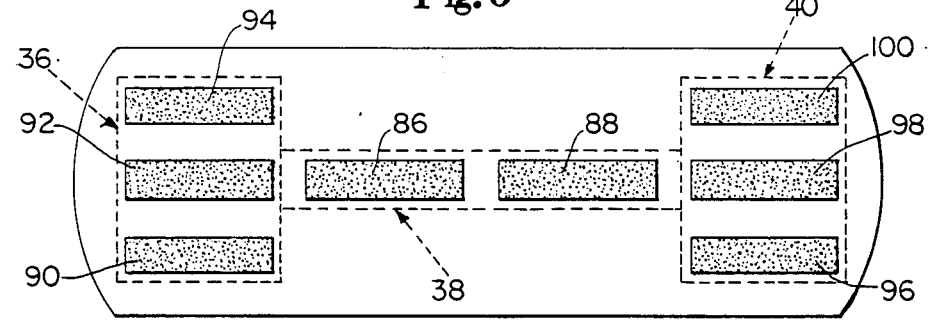
FIG. 6 is a bottom plan view of a still further alternative embodiment of the absorbent article of the present invention.

FIG. 6 shows a still further alternative embodiment of the sanitary napkin of the present invention. The stem adhesive portion 38 comprises interrupted spaced adhesive strips 86 and 88 that extend longitudinally along the sanitary napkin. The base adhesive portion 36 and the head adhesive portion 40 each comprises three strips of adhesive 90, 92, 94, and 96, 98, 100, respectively, that extend longitudinally along the sanitary napkin.

While particular embodiments of the present invention have been illustrated and described, those skilled in the art will recognize that various changes and modifications can be made without departing from the spirit and scope of the invention. It is intended to cover, in the claims, all such modifications that are within the scope of this invention.

What is claimed is:

1. An absorbent article designed to be worn in the crotch region of a garment, the absorbent article having a central region, a first end region and a second end region, the absorbent article comprising:
    an absorbent core;
    a backsheet associated with said absorbent core; and
    adhesive attachment means disposed on said backsheet for securing the absorbent article to a garment, said adhesive attachment means consisting of an adhesive pattern having the shape of a block I having
        a base adhesive portion located in said first end region of the absorbent article,
        a stem adhesive portion centrally located in said central region of the absorbent article, and
        a head adhesive portion located in said second end region of the absorbent article.

2. The absorbent article of claim 1 wherein said head adhesive portion and said base adhesive portion of said adhesive attachment means each comprises a strip of adhesive that extends transversely across the absorbent article.

3. The absorbent article of claim 1 wherein said head adhesive portion and said base adhesive portion of said adhesive attachment means each comprises at least two strips of adhesive that extend transversely across the absorbent article.

4. An absorbent article designed to be worn in the crotch of a garment, the absorbent article having a central region, a first end region and a second end region, the absorbent article comprising:
    an absorbent core;
    a backsheet associated with said absorbent core; and
    adhesive attachment means disposed on said backsheet for securing the absorbent article to a garment, said adhesive attachment means consisting of an adhesive pattern having the shape of a block I having
        a base adhesive portion located in said first end region of the absorbent article,
        a stem adhesive portion centrally located in said central region of the absorbent article,
        a head adhesive portion located in said second end region of the absorbent article, and
        said head adhesive portion and said base adhesive portion of said adhesive attachment means each comprising at least two strips of adhesive that extend longitudinally along the absorbent article.

5. The absorbent article of claim 1 wherein said stem adhesive portion of said adhesive attachment means comprises a line of adhesive.

6. The absorbent article of claim 5 wherein said head adhesive portion and said base adhesive portion of said adhesive attachment means each comprises a strip of adhesive that extends transversely across the absorbent article.

7. The absorbent article of claim 5 wherein said head adhesive portion and said base adhesive portion of said adhesive attachment means each comprises at least two strips of adhesive that extend transversely across the absorbent article.

8. An absorbent article designed to be worn in the crotch region of a garment, the absorbent article having a central region, a first end region and a second end region, the absorbent article comprising:
    an absorbent core;
    a backsheet associated with said absorbent core; and
    adhesive attachment means disposed on said backsheet for securing the absorbent article to a garment, said adhesive attachment means consisting of an adhesive pattern having the shape of a block I having
        a base adhesive portion located in said first end region of the absorbent article,
        a stem adhesive portion centrally located in said central region of the absorbent article, said stem adhesive portion of said adhesive attachment means comprising a line of adhesive,
        a head adhesive portion located in said second end region of the absorbent article, and
        said head adhesive portion and said base adhesive portion of said adhesive attachment means each comprising at least two strips of adhesive that extend longitudinally along the absorbent article.

9. The absorbent article of claim 1 wherein said stem adhesive portion of said adhesive attachment means comprises discrete spaced strips of adhesive.

10. The absorbent article of claim 9 wherein said head adhesive portion and said base adhesive portion of said adhesive attachment means each comprises a strip of adhesive that extends transversely across the absorbent article.

11. The absorbent article of claim 9 wherein said head adhesive portion and said base adhesive portion of said adhesive attachment means each comprises at least two strips of adhesive that extend tranversely across the absorbent article.

12. The absorbent article of claim 9 wherein said head adhesive portion and said base adhesive portion of said adhesive attachment means each comprises at least two strips of adhesive that extend longitudinally along the absorbent article.

13. The absorbent article of claim 1 wherein said base adhesive portion and said head adhesive portion each comprises a generally rectangular zone extending transversely across the respective end region in which each is located wherein the area of said zone comprises at least about fifty percent of the effective adhesive area of each respective end region.

14. The absorbent article of claim 13 wherein said base adhesive portion and said head adhesive portion are each located so as to be equidistantly inwardly spaced from the longitudinal edges of the absorbent article.

15. The absorbent article of claim 14 wherein said base adhesive portion and said head adhesive portion are each equidistantly inwardly spaced about 6 mm from the longitudinal edges of the absorbent article.

16. The absorbent article of claim 1 wherein said stem adhesive portion comprises a narrow rectangular zone extending longitudinally in the central region of the absorbent article wherein the area of said zone comprises less than about 50% of the effective adhesive area of said central region.

17. The absorbent article of claim 16 wherein the area of said zone comprises less than about 30% of the total effective adhesive area of said central region.

18. The absorbent article of claim 16 wherein said stem adhesive portion is located so as to be equidistantly inwardly spaced from the longitudinal edges of the absorbent article.

19. The absorbent article of claim 18 wherein said stem adhesive portion is equidistantly inwardly spaced about 18 mm from the narrowest point of each longitudinal edge of the absorbent article.

20. The absorbent article of claim 1 wherein said base adhesive portion, stem adhesive portion and head adhesive portion each comprise an array of discrete adhesive elements.

* * * * *

UNITED STATES PATENT AND TRADEMARK OFFICE
CERTIFICATE OF CORRECTION

PATENT NO. : 4,690,680

DATED : September 1, 1987

INVENTOR(S) : Maureen L. Higgins

It is certified that error appears in the above-identified patent and that said Letters Patent is hereby corrected as shown below:

In Column 5 at line 36: delete "imprevious" and insert -- impervious--.

In Column 7 at line 15: insert at the end of line 15 these previously omitted words -- portions. While the size, arrangement and disposition of adhesive --.

Signed and Sealed this

Fifth Day of April, 1988

Attest:

Attesting Officer

DONALD J. QUIGG

Commissioner of Patents and Trademarks